(12) United States Patent
Giuliani et al.

(10) Patent No.: US 10,278,909 B2
(45) Date of Patent: May 7, 2019

(54) COMPOSITION SUITABLE TO PRESERVE THE PHYSIOLOGICAL CONDITION OF SKIN AND HAIR AND REESTABLISH THEIR REGENERATIVE FUNCTIONS

(71) Applicant: GIULIANI S.P.A., Milan (IT)

(72) Inventors: Giammaria Giuliani, Milan (IT); Anna Benedusi, Milan (IT); Barbara Marzani, Carbonara al Ticino (IT); Antonio Mascolo, Milan (IT); Antonio Limitone, Milan (IT)

(73) Assignee: Giuliani S.P.A., Milan (IT)

( * ) Notice: Subject to any disclaimer, the term of this patent is extended or adjusted under 35 U.S.C. 154(b) by 0 days.

(21) Appl. No.: 15/321,121

(22) PCT Filed: Jun. 25, 2015

(86) PCT No.: PCT/EP2015/064362
§ 371 (c)(1),
(2) Date: Dec. 21, 2016

(87) PCT Pub. No.: WO2015/197759
PCT Pub. Date: Dec. 30, 2015

(65) Prior Publication Data
US 2017/0135928 A1    May 18, 2017

(30) Foreign Application Priority Data
Jun. 26, 2014 (IT) ................ MI2014A1161

(51) Int. Cl.
| | | |
|---|---|---|
| *A61K 8/02* | (2006.01) | |
| *A61K 8/44* | (2006.01) | |
| *A61K 8/49* | (2006.01) | |
| *A61Q 5/00* | (2006.01) | |
| *A61Q 5/02* | (2006.01) | |
| *A61Q 7/00* | (2006.01) | |
| *A23L 33/15* | (2016.01) | |
| *A23L 33/16* | (2016.01) | |
| *A61Q 19/00* | (2006.01) | |
| *A61Q 19/08* | (2006.01) | |
| *A23L 33/105* | (2016.01) | |
| *A23L 33/175* | (2016.01) | |
| *A61K 31/198* | (2006.01) | |
| *A61K 31/205* | (2006.01) | |
| *A61K 31/522* | (2006.01) | |
| *E06B 9/52* | (2006.01) | |

(52) U.S. Cl.
CPC ......... *A61K 8/4953* (2013.01); *A23L 33/105* (2016.08); *A23L 33/15* (2016.08); *A23L 33/16* (2016.08); *A23L 33/175* (2016.08); *A61K 8/0204* (2013.01); *A61K 8/44* (2013.01); *A61K 31/198* (2013.01); *A61K 31/205* (2013.01); *A61K 31/522* (2013.01); *A61Q 5/006* (2013.01); *A61Q 5/02* (2013.01); *A61Q 7/00* (2013.01); *A61Q 19/00* (2013.01); *A61Q 19/08* (2013.01); *E06B 9/52* (2013.01); *A23V 2002/00* (2013.01); *A61K 2800/5922* (2013.01); *A61K 2800/92* (2013.01); *E06B 2009/527* (2013.01)

(58) Field of Classification Search
CPC ........ A23L 33/105; A23L 33/15; A23L 33/16; A23L 33/175; A23V 2002/00; A61K 2800/5922; A61K 2800/92; A61K 8/0204; A61K 8/44; A61K 8/4953; A61K 31/198; A61K 31/205; A61K 31/522; A61Q 19/00; A61Q 19/08; A61Q 5/006; A61Q 5/02; A61Q 7/00
USPC ................................................ 514/1, 263.31
See application file for complete search history.

(56) References Cited

U.S. PATENT DOCUMENTS

| | | | | |
|---|---|---|---|---|
| 7,645,742 B2 * | 1/2010 | Stohs | ...................... | A61K 31/19 424/94.1 |
| 7,790,768 B2 * | 9/2010 | Gan | .......................... | A61K 8/44 514/564 |
| 7,854,939 B2 * | 12/2010 | Longo | .................... | A61K 8/042 424/401 |
| 8,232,317 B2 * | 7/2012 | Gan | .......................... | A61K 8/44 514/564 |

(Continued)

FOREIGN PATENT DOCUMENTS

| | | |
|---|---|---|
| EP | 1800654 A2 | 6/2007 |
| JP | 2000319177 A | 11/2000 |

(Continued)

OTHER PUBLICATIONS

Murosaki et al., "A Combination of Caffeine, Arginine, Soy Isoflavones, and L-Carnitine Enhances Both Lipolysis and Fatty Acid Oxidation in 3T3-L1 and HepG2Cells in Vitro and in KKMice in Vivo", 2007, The Journal of Nutrition, 137(10), pp. 2252-2257. (Year: 2007).*

(Continued)

*Primary Examiner* — My-Chau T. Tran
(74) *Attorney, Agent, or Firm* — Pepper Hamilton LLP

(57) ABSTRACT

The present invention relates to a composition for pharmaceutical, nutritional or cosmetic use, suitable to preserve the physiological condition and health of skin and hair and to reestablish their regenerative functions, characterized in that it comprises a mixture of carnitine, caffeine and arginine as active principle, as such or as derivatives, such as pharmacologically acceptable salts. The effect of preserving the physiologic condition and health of skin and hair, and of reestablishing their regenerative functions is mainly achieved through an increase in ATP production by skin and hair cells.

13 Claims, 1 Drawing Sheet

(56) References Cited

U.S. PATENT DOCUMENTS

| | | | |
|---|---|---|---|
| 8,506,942 B2 * | 8/2013 | Burry | A61K 8/44 424/74 |
| 2006/0292134 A1 | 12/2006 | Stohs | |
| 2011/0064712 A1 | 3/2011 | Amato | |
| 2013/0209551 A1 * | 8/2013 | Luthy | A61K 47/48038 424/450 |
| 2015/0306023 A1 * | 10/2015 | Domloge | A61Q 19/06 424/757 |

FOREIGN PATENT DOCUMENTS

| | | |
|---|---|---|
| WO | 2007/003307 A1 | 1/2007 |
| WO | 2012/042010 A1 | 4/2012 |

OTHER PUBLICATIONS

International Search Report and Written Opinion for corresponding Application No. PCT/EP2015/064362, filed Jun. 25, 2015 (dated Oct. 21, 2015).
International Preliminary Report on Patentability for corresponding Application No. PCT/EP2015/064362, filed Jun. 25, 2015 (dated Aug. 17, 2016).

* cited by examiner

COMPOSITION SUITABLE TO PRESERVE THE PHYSIOLOGICAL CONDITION OF SKIN AND HAIR AND REESTABLISH THEIR REGENERATIVE FUNCTIONS

This application is a national stage application under 35 U.S.C. § 371 of PCT Application No. PCT/EP2015/064362, filed Jun. 25, 2015, which claims priority of Italy Application No. MI2014A001161, filed Jun. 26, 2014, which are hereby incorporated by reference in their entirety.

FIELD OF THE INVENTION

The present invention relates to a pharmaceutical, nutritional or cosmetic composition suitable to preserve the physiological condition and health of skin and hair, and to reestablish their regenerative functions.

BACKGROUND ART

It is known that in cell energy metabolism, adenosine triphosphate (ATP), a nucleotide consisting of ribose sugar, adenine base and three phosphate groups and produced in mitochondria by cellular respiration, contains a large amount of energy stored in chemical bonds and for this reason plays a role of paramount importance. Such bonds are highly unstable and, when hydrolyzed, they release a large amount of energy (about 7 kcal/mol) available for vital cell functions.

In addition to providing energy, ATP has other essential roles within cells: it is required for the synthesis of DNA in the process of replication and RNA for protein synthesis, it regulates important biochemical pathways in muscle contraction, active transport of nutrients and ions, maintenance of osmosis, cellular division, regeneration and healing, synthesis of collagen and elastin. It is also used as a substrate of kinases which phosphorylate proteins and lipids, and as adenylate cyclase to produce cyclic AMP. Therefore, ATP is considered a fundamental molecule in cell energy metabolism by biologists.

As in all tissues, in particular skin and hair cells need energy to preserve the vital functions and the ability to regenerate and repair themselves, and to grow. More specifically, the hair follicle has the ability to renew and regenerate itself through different cyclical phases, and this biological and functional complexity requires a large energy consumption.

There are situations where the production of ATP decreases to the expense of the cellular functionality first, and tissues later. Such situations include, for example, cellular aging, where a decline in the mitochondrial function occurs with increased production of free radicals (ROS), which in turn cause damage to mitochondria, further compromising the functionality thereof, or the action of ionizing radiation and ultraviolet radiation which, causing damage to the cells, directly alter the structures of DNA and proteins with production of ROS and of reactive carbonyl species, such processes modifying the cellular energy metabolism at multiple levels, as reported in the literature, see for example Jacobson, Gamal, Roberts, Wondrak, Jacobson: Optimizing the energy status of skin cells during solar radiation, Journal of Photochemistry and Photobiology B: Biology 63 (2001) 141-147.

Energy is essential in the metabolism of all cell types, and in particular those of the hair follicle in order to preserve the functionality thereof by supporting the active phase of the follicle characterized by significant cellular proliferation, as well as the remodeling phase in the life cycle of hair. In the case of alopecia, energy production is affected by factors such as stress, hyper-production of dihydrotestosterone DHT, exposure to environmental factors which inhibit the cellular energy metabolism causing a chronic deficiency of ATP.

K. Adachi et Al., Human Hair Follicles: Metabolism and Control Mechanisms, J. Soc. Cosmet. Chem., 21, 901-924 (1970) studies molecular bases for the etiologic factors of common baldness and the pathways of energy producing systems, to examine the changes in these pathways during the different functional stages of the hair follicles. By observing that during the growing stage (anagen) of the hair cycle, the follicles develop; when hair is formed by the matrix of the follicle, growth ceases, and the follicle is in the resting stage (telogen), and after a specific period of quiescence these processes resume autonomously, Adachi reckons that as far as the energy requirement is concerned, one can assume that the growing hair follicles synthesizing keratin require much more energy than the resting ones, and that the growing hair follicles utilize glucose about twice as fast as the resting follicles. Thus, the pathways to yield ATP should be accelerated to meet such requirements.

K. Shorter et al., Human hair follicles contain two forms of ATP-sensitive potassium channels only one of which is sensitive to minoxidil, FASEB J., 22, No. 6, 1725-1736 (2008) discloses that, in the mechanism of the known minoxidil activity against balding, human follicular dermal papillae contain K-ATP (ATP-sensitive potassium) channels that can respond to minoxidil, thus indicating a further relationship between ATP and hair growth.

US2003093915 describes an apparatus and method for stimulating hair growth based on laser light penetrating into soft tissue and increasing the action of ATP as a major carrier of energy from one reaction site to another in living cells. By doing so, laser light is said to increase the energy available to cells so as to take in nutrients faster and get rid of waste products.

It is the object of the present invention to provide a means for preserving and optimizing the cell energy condition by counteracting the negative effects due to the decrease of ATP induced, for example and typically, by an inadequate diet, metabolism alterations, cellular aging or by the action of UV radiation on the skin. In particular, it is the object of the present invention to provide a means for preserving and optimizing the energy condition of skin and hair cells, so as to preserve the physiological status and health thereof, and reestablishing their regenerative functions.

SUMMARY OF THE INVENTION

These objects and other advantages that can be inferred hereafter in the present description are achieved by means of a composition for pharmaceutical, nutritional or cosmetic use suitable to preserve the physiological condition and health of skin and hair and to reestablish their regenerative functions, characterized in that it comprises a mixture of caffeine, carnitine and arginine as active principle.

In particular, the mixture according to the invention is suitable to contrast hair loss and promote hair regrowth.

DESCRIPTION OF THE INVENTION

As demonstrated by an experimental study described hereafter in the present description, the effect of preserving the physiologic condition and health of skin and hair, and of reestablishing their regenerative functions according to the invention is achieved through an increase in ATP production by skin and hair cells.

According to the present invention, by carnitine and arginine it is preferably meant the enantiomer L-carnitine and L-arginine.

Carnitine and arginine may be used as such or as pharmaceutically acceptable derivatives thereof, such as salts or simple esters. By way of a non limiting example, among salts are hydrochloride, dihydrochloride, aspartate, PCA (pyrrolidone carboxylic acid), tartrate, fumarate; and among simple esters is acetylcarnitine.

A composition of the invention may be formulated both for topical use, and for oral and systemic use. Every common pharmaceutical form is suitable for the two types of administration. In particular, among the suitable pharmaceutical forms for oral use, modified release tablets are preferred.

Preferably, in a composition according to the invention, carnitine, caffeine, arginine are present in a ratio by weight of 1:1:3, respectively. By way of example, a composition is cited according to the following concentrations: carnitine 10 mg/ml, caffeine 10 mg/ml, arginine 30 mg/ml.

More preferably, a composition of the invention is characterized in that it comprises as active principle a mixture of carnitine, caffeine and arginine according to the following concentrations: in the case of products for topical use, carnitine from 1.0 to 33.3 mg/ml, caffeine from 1.0 to 33.3 mg/ml, arginine from 3 to 100 mg/ml; even more preferably: carnitine 2-10 mg/ml, caffeine 2-10 mg/ml, arginine 6-30 mg/ml. In the case of products for oral and systemic use, a daily administration within the following dosage ranges is preferable: carnitine 4-400 mg, caffeine 4-400 mg, arginine 12-1200 mg. More preferably: carnitine 10-100 mg, caffeine 10-100 mg, arginine 30-300 mg.

According to an embodiment, the composition of the invention is specifically aimed at preserving the physiological condition and health of the skin, and at reestablishing the regenerative functions of the skin.

According to a different embodiment, the composition of the invention is specifically aimed at preserving the physiological condition and health of hair, and at reestablishing the regenerative functions of hair. In particular, the mixture according to the invention is suitable to contrast hair loss and promote hair regrowth.

The present invention also relates to the cosmetic use of a mixture of carnitine, caffeine and arginine as defined above for preserving the physiological condition and health of skin and hair, and for reestablishing their regenerative functions.

EXAMPLES

The following are non limiting examples of a composition particularly suitable for the uses specified above. The component quantities are expressed in milligrams or in g/100 mL.

Example 1

Modified release TABLETS to contrast hair loss and promote regrowth

| COMPONENT | quantity (mg) |
|---|---|
| d-Biotin | 0.05 |
| *Ajuga reptans* dry extract | 2.5 |
| Arginine monohydrochloride | 180 |
| Zinc (as liposomal zinc) | 15 |
| Ubidecarenone | 10 |
| Acetyl L-carnitine hydrochloride | 70 |
| Creatine monohydrate | 170 |
| Green coffee dry extract | 50 |
| Caffeine | 50 |
| Pomegranate dry extract | 50 |
| Microcrystalline cellulose | 100 |
| Calcium phosphate | 70 |
| Hydroxypropyl methylcellulose | 45 |
| Magnesium stearate | 8 |
| Silicon dioxide | 4 |

Example 2

LOTION to contrast hair loss and promote regrowth

| COMPONENT | quantity (g/100 ml) |
|---|---|
| Denat. alcohol type C | 10-20 |
| Betaine | 0.01-0.1 |
| Citric acid | 0.5-3.0 |
| CG-Fibramin (Oligopeptide-42) | 1-3 |
| Mannitol | 0.5-1.5 |
| Potassium octatrienoate | 0.1-1 |
| PEG-40 Hydrogenated castor oil | 0.1-0.5 |
| Perfum | 0.1-0.5 |
| VP/VA Copolymer | 0.01-0.05 |
| Tartrazine yellow (CI 19140) | 0.0001-0.0003 |
| Carnitine | 0.25-0.75 |
| Caffeine | 0.25-0.75 |
| Arginine | 0.75-2.25 |
| Water | as needed to 100 mL |

Example 3

MOUSSE to contrast hair loss and promote regrowth

| COMPONENT | quantity (g/100 ml) |
|---|---|
| Denatured ethyl alcohol type C | 5-15 |
| Taurine | 1-3 |
| Sodium olivamphoacetate | 0.5-1.5 |
| Polyoxyethylene hydrogenated castor oil | 0.5-1.5 |
| Parfum | 0.25-1 |
| Citric acid | 0.1-1 |
| Calcium D-pantothenate | 0.1-0.5 |
| PEG-40 Hydrogenated castor oil | 0.1-0.3 |
| Disodium EDTA dihydrate | 0.04-0.08 |
| Polyquaternium-16 | 0.02-0.06 |
| Potassium metabisulfite | 0.01-0.03 |
| *Vitis vinifera* seed extract | 0.005-0.015 |
| Biotin | 0.002-0.006 |
| Arginine | 0.075-0.225 |
| Tocopherol | 0.0005-0.0015 |
| Carnitine | 0.025-0.075 |
| Caffeine | 0.025-0.075 |
| Water | as ndeeded to 100 ml |

Example 4

Food supplement tablets to contrast hair loss and promote regrowth

| COMPONENT | quantity (mg) |
| --- | --- |
| L-Arginine monohydrochloride | 240-360 |
| Microcrystalline cellulose | 100-200 |
| Calcium phosphate dibasic dihydrate | 75-175 |
| Borage seed oil powder | 50-150 |
| Caffeine | 66.6-100 |
| Acetyl L-carnitine hydrochloride | 100-150 |
| Hydroxypropylmethylcellulose K100 | 20-60 |
| Zinc bisglycinate 28.2% | 10-40 |
| Hydroxypropylmethylcellulose | 10-40 |
| White filming polymer | 5-25 |
| Rutin | 5-25 |
| Calcium D-pantothenate | 5-15 |
| Mono- and diglycerides of fatty acids | 15-5 |
| Silicon dioxide (colloidal silica) | 5-15 |
| Copper bisglycinate 30% | 2-6 |
| Vegetable stearic acid | 3-5 |
| Spermidine trihydrochloride | 0.25-0.75 |
| Biotin | 0.1-0.3 |

Example 5

Food supplement tablets to contrast hair loss and promote regrowth

| COMPONENT | quantity (mg) |
| --- | --- |
| Granular L-methionine Matris | 200-400 |
| Coated vitamin C | 50-100 |
| Microcrystalline cellulose 200 | 50-100 |
| *Vitis vinifera* dry seed extract | 50-100 |
| Arginine monohydrochloride | 61.2-82.8 |
| Calcium phosphate dibasic dihydrate | 20-40 |
| Caffeine | 17-23 |
| Acetyl L-carnitine hydrochloride | 25-35 |
| Vitamin E acetate 50% | 10-20 |
| Silicon dioxide (colloidal silica) | 10-20 |
| Olive tree (*Olea Europaea* l.) leave dry extract | 5-15 |
| Calcium D-pantothenate | 5-10 |
| Vegetable magnesium stearate | 5-10 |
| Zinc (as bisglycinate) | 5-10 |
| Macrogol 4000 (PEG-4000) | 2-5 |
| Vitamin B6 (pyridoxine hydrochloride) | 2-3 |
| Rutin | 2-3 |
| Vegetable zeaxanthin 5% | 1-5 |
| Vegetable stearic acid (E570) | 1-3 |
| Copper (as bisglycinate) | 1-2 |
| Hyaluronic acid | 0.5-1.5 |
| Cross-linked sodium carboxymethylcellulose | 0.5-1.5 |
| Spermidine trihydrochloride | 0.25-0.75 |
| Hydroxypropylmethylcellulose K100 | 0.25-0.75 |
| Sodium alginate | 0.25-0.75 |
| Folic acid | 0.1-0.3 |
| Selenium yeast 2000 ppm | 0.02-0.1 |
| Biotin | 0.025-0.075 |

Example 6

Dandruff SHAMPOO which contrasts hair loss and promotes regrowth

| COMPONENT | quantity (mg) |
| --- | --- |
| Potassium undecylenoyl hydrolyzed wheat protein | 10-20 |
| Rewoderm LI S 80 | 3-5 |
| Zinc coceth sulfate | 2-4 |
| Disodium laureth sulfosuccinate | 2-4 |
| PEG-200 Hydrogenated glyceryl palmate | 1-3 |
| Sodium lauroyl sarcosinate | 1-2 |
| Citric acid | 0.5-1.5 |
| Betaine | 0.5-1.5 |
| Cocamide MIPA | 0.5-1.5 |
| Inositol | 0.5-1.5 |
| Xylitol | 0.5-1.5 |
| PEG-7 Glyceryl cocoate | 0.5-1.5 |
| Laureth-3 | 0.4-0.8 |
| Perfum | 0.5-1 |
| L-Arginine | 0.4-0.8 |
| Taurine | 0.25-0.75 |
| PEG-90 Glyceryl isostearate | 0.2-0.6 |
| Polyoxyethylene hydrogenated castor oil | 0.2-0.4 |
| Piroctone olamine | 0.2-0.4 |
| Polyquaternium-10 | 0.2-0.4 |
| Disodium EDTA dihydrate | 0.1-0.3 |
| Carnitine | 0.13-0.27 |
| Caffeine | 0.13-0.27 |
| Laureth-2 | 0.05-0.1 |
| Phenyl trimethicone | 0.04-0.08 |
| Silicone quaternium-17 | 0.02-0.06 |
| Laureth-4 | 0.02-0.06 |
| Laureth-23 | 0.01-0.03 |
| Water | as needed to 100 |

Example 7

Anti-aging cream

| COMPONENT | quantity (%) |
| --- | --- |
| Disodium EDTA | 0.05-0.15 |
| Phenoxyethanol | 0.5-1.0 |
| O-cymen-5-ol | 0.01-0.1 |
| Glyceryl | 0.5-4.0 |
| Propanediol | 0.5-4.0 |
| Citric acid | 0.05-2.0 |
| Cetearyl olivate | 0.1-7.0 |
| sorbitan olivate | 0.1-5.0 |
| Cetyl palmitate | 0.1-2.0 |
| Isononyl Isononanoate | 0.1-3.0 |
| Caprylic/capric triglycerides | 0.5-5.0 |
| Octyldodecanol | 0.5-5.0 |
| Glycyrrhetinic acid | 0.01-0.2 |
| Oleyl erucate | 0.5-2.0 |
| Hydrogenated polidecene | 0.1-3.0 |
| Sorbityl furfural | 0.01-0.3 |
| Sodium hyaluronate high polymerization degree | 0.01-0.5 |
| Sodium hyaluronate low polymerization degree | 0.01-0.5 |
| *Argania spinosa* kernel oil (Ultra Refined) | 0.5-1.5 |
| Dimethicone | 0.1-1 |
| Cyclopentasiloxane | 0.10-2.0 |
| Parfum | 0.1-0.5 |
| Xanthan gum | 0.01-0.50 |
| Carnitine | 0.13-0.27 |
| Caffeine | 0.13-0.27 |
| L-Arginine | 0.4-0.8 |
| Water | as needed to 100 |

Example 8

Food supplement tablets to contrast hair loss and promote regrowth

| COMPONENT | quantity (mg) |
| --- | --- |
| d-Biotin | 0.05 |
| *Ajuga reptans* dry extract | 2.5 |
| L-Arginine monohydrochloride | 180 |
| Zinc (as liposomal zinc) | 15 |
| Ubidecarenone | 10 |
| L-Carnitine L-Tartrate | 150 |

-continued

| COMPONENT | quantity (mg) |
| --- | --- |
| Creatine monohydrate | 170 |
| Green coffee dry extract | 50 |
| Caffeine | 50 |
| Pomegranate dry extract | 50 |
| Microcrystalline cellulose | 100 |
| Calcium phosphate | 70 |
| Hydroxypropyl methylcellulose | 45 |
| Magnesium stearate | 8 |
| Silicon dioxide | 4 |

DRAWINGS

THE diagrams according to the figures in the accompanying drawings show the results for the experimental study described hereafter.

EXPERIMENTAL STUDY: ATP ASSAY

Materials and Methods
Cells

Human Hair Follicle Outer Root Sheath Cells (HHFORSC), supplied by Innoprot, are isolated by ScienCell Research Labs from the outer sheath of the root of human hair.

The cell line was grown in culture medium for mesenchymal stem cells (MSCM): 500 mL basal medium, 20% fetal bovine serum (FBS), 1% growth supplement for mesenchymal stem cells (MSCGS), 1% penicillin/streptomycin (P/S solution) and maintained in 25 $cm^2$ culture flasks at 37° C. and 5% $CO_2$.

Before proceeding with plating the cells, the flask cells is coated with poly-L-lysine (2 μg/$cm^2$).

Every two days, the confluent cultures are divided 1:3-1:6, after washing with DPBS (Dulbecco's Phosphate-Buffered Saline), using a solution of T/E (trypsin/EDTA solution) and TNS (Trypsin Neutralization Solution) and seeded at 2-5×$10^4$ cell/$cm^2$, 37° C., 5% $CO_2$.

Treatments and ATP Assay
Experimental Procedure
Day 1: Seed Cells

When the cells (HHFORSC) reach about 80% confluence, they are detached with trypsin/EDTA and seeded at a density of 1×$10^6$ cells/ml in 12-well plates and then incubated at 37° C., 5% $CO_2$ (24 h).

Day 2: chemical treatment for 24 h

When the cells reach about 80% confluence, they are treated with samples of the following compounds or mixtures of compounds, tested at the concentrations described hereafter:

Carnitine 10 mg/ml
Caffeine 10 mg/ml
Arginine 30 mg/ml
Carnitine 10 mg/ml+Caffeine 10 mg/ml
Carnitine 10 mg/ml+Arginine 30 mg/ml
Caffeine 10 mg/ml+Arginine 30 mg/ml
Carnitine 10 mg/ml+Caffeine 10 mg/ml+Arginine 30 mg/ml The cells treated with culture medium only were used as control.

All the cells were incubated at 37° C., 5% $CO_2$ for 24 h.

After 24 hours of treatment, the cells were washed with cold DPBS and resuspended in buffer for the ATP assay with protease inhibitor (1%). The samples were then lysed by pipetting repeatedly and centrifuged to remove insoluble materials, and finally stored on ice until use.

The reaction mixture for ATP was prepared by mixing ATP Assay Buffer (88%), ATP Probe (4%), ATP Converter (4%) and Developer Mix (4%). 0.5 ml of reaction mixture of ATP were added to each 24-well plate and 50 μl of each sample were added. The standard curve (0.04-0.08-0.12-0.16-0.2 mM) was set as reported in the ATP-assay kit Abcam (Abcam, Cambridge, UK).

The samples were incubated at room temperature for 30 minutes, in the dark. The absorbance was read at a wavelength of 570 nm with a reference filter of 630 nm in a microplate reader Biotek ELX808 using a predetermined protocol and after having correctly defined a layout of the plate.

The ATP concentration was calculated by interpolating the data of the standard curve after subtraction of the blank:

$$[ATP] \text{ (nmol/μl)} = Ts/Sv$$

where Ts is the amount of ATP from the standard curve (nmol); SV is the volume of the sample (before dilution) added to the sample wells (μl).

Figure 1:
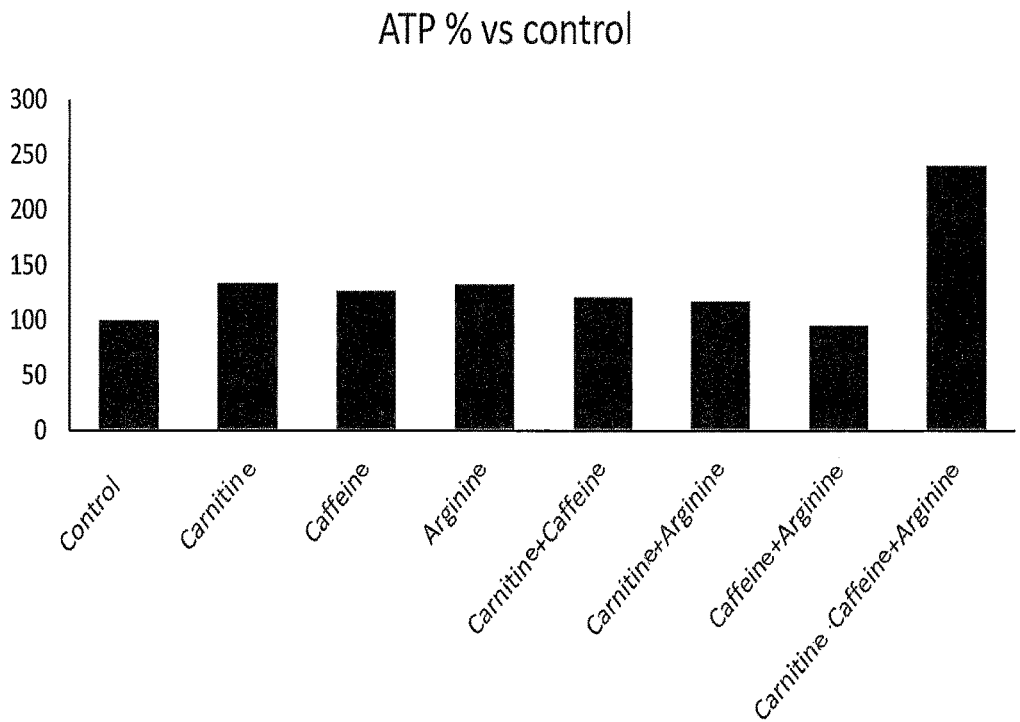
FIG. 1 shows a diagram for the production of cellular ATP for the mixture of the invention compared with other reference products.
Figure 2:
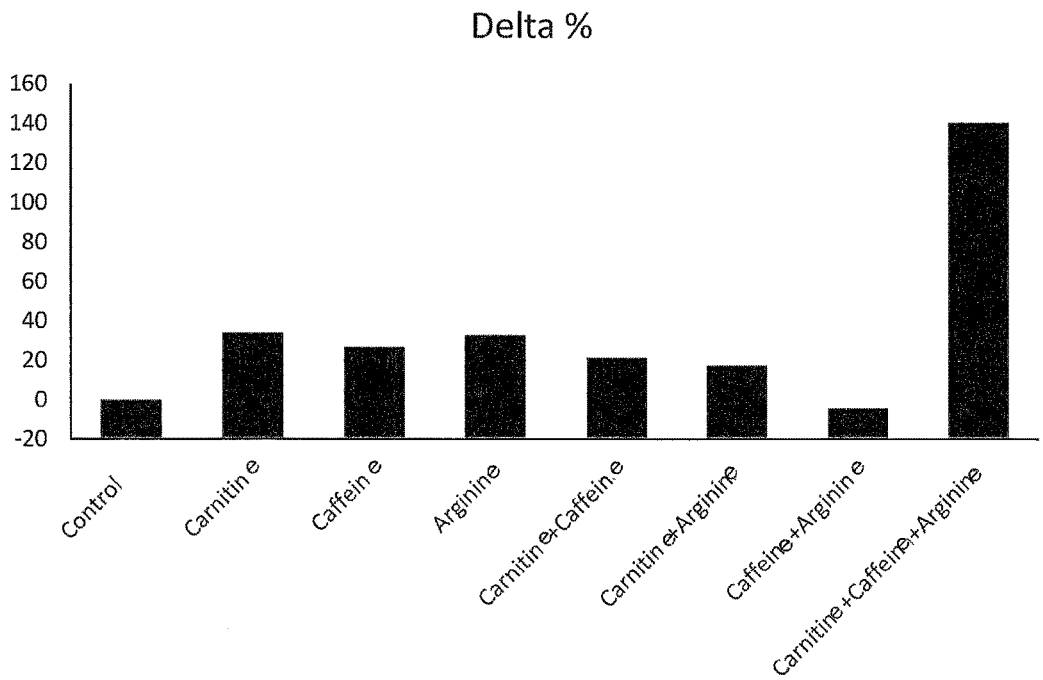
FIG. 2 shows a diagram of the corresponding increase Δ% in the production of cellular ATP.

The following results were obtained, also graphically represented in FIGS. 1 and 2:

Results

| Sample | ATP % vs control | Δ % |
| --- | --- | --- |
| Control | 100.00 | / |
| Carnitine | 134.16 | 34.164 |
| Caffeine | 126.84 | 26.843 |
| Arginine | 132.94 | 32.944 |
| Carnitine + Caffeine | 121.35 | 21.352 |
| Carnitine + Arginine | 117.39 | 17.387 |
| Caffeine + Arginine | 95.73 | −4.270 |
| Carnitine + Caffeine + Arginine | 240.31 | 140.315 |

The results show that the only combination of active ingredients capable of providing a surprising increase Δ% in the production of cellular ATP compared to that achieved with the individual ingredients is selectively that consisting of carnitine+caffeine+arginine, for which the ATP production increases by more than 140% compared to the untreated control.

The result proves to be surprising especially compared to the case of the tested pairs carnitine+caffeine, carnitine+arginine, caffeine+arginine, for which an increase Δ% in the ATP is found which is lower than that obtained with the individual ingredients, in one case even negative. This demonstrates that the selection of the triad according to the invention is such as to provide a result of ATP activity which is certainly unexpected and abnormal in comparison with the possible combinations of the same components in pairs.

The experimental data thus show an unexpected synergy behavior in the ATP activity of the selective combination carnitine+caffeine+arginine, such as to propose an advantageous use thereof in the pharmaceutical or cosmetic field for any skin and hair treatment which requires an enhanced contribution of cellular energy, through the administration of a suitable composition with directions typically defined in the industry as "energy boosters".

Also in view of the background art mentioned above describing a relationship between high levels of cellular ATP and inhibition of hair loss and/or stimulation of hair growth, as well as skin health, the compositions according to the present invention are particularly indicated for such uses in humans.

The invention claimed is:

1. A mixture of carnitine, caffeine and arginine, or pharmacologically acceptable salts or simple esters thereof, as active principle in a nutritional or cosmetic composition for preserving the physiological condition and health of skin or hair and for reestablishing their regenerative functions, wherein the ratio by weight of carnitine, caffeine, and arginine in the mixture is 1:1:3, respectively.

2. The mixture according to claim 1, wherein the mixture is made of carnitine, caffeine and arginine as active principle according to the following concentrations: carnitine 10 mg/ml, caffeine 10 mg/ml, arginine 30 mg/ml.

3. The mixture according to claim 1 for topical administration, wherein the mixture is made of carnitine, caffeine, arginine as active principle according to the following concentrations: carnitine from 1.0 to 33.3 mg/ml, caffeine from 1.0 to 33.3 mg/ml, arginine from 3 to 100 mg/ml.

4. The mixture according to claim 3, wherein the mixture is made of carnitine, caffeine and arginine as active principle according to the following concentrations: carnitine 2-10 mg/ml, caffeine 2-10 mg/ml, arginine 6-30 mg/ml.

5. The mixture according to claim 1 for oral and systemic administration, wherein the mixture is made of carnitine, caffeine, arginine as active principle according to a daily administration dose within the following ranges: carnitine 4-400 mg, caffeine 4-400 mg, arginine 12-1200 mg.

6. The mixture according to claim 5, wherein the mixture is made of carnitine, caffeine, arginine as active principle according to a daily administration dose within the following ranges: carnitine 10-100 mg, caffeine 10-100 mg, arginine 30-300 mg.

7. A method for preserving the physiological condition and health of skin or hair, or for reestablishing their regenerative functions in a subject in need thereof, said method comprising:

administering, to the subject, a mixture of carnitine, caffeine and arginine, or pharmacologically acceptable salts or simple esters thereof, wherein the ratio by weight of carnitine, caffeine, and arginine in the mixture is 1:1:3, respectively, and wherein said administering is carried out at a dose effective to preserve the physiological condition and health of the subject's skin or hair or reestablish their regenerative functions in said subject.

8. The method according to claim 7, wherein said administering is carried out at a dose effective to preserve the physiological condition and health of the subject's skin.

9. The method according to claim 7, wherein said administering is carried out at a dose effective to preserve the physiological condition and health of the subject's hair.

10. The method according to claim 9, wherein said administering is carried out at a dose effective to contrast hair loss in the subject.

11. The method according to claim 9, wherein said administering is carried out at a dose effective to promote hair regrowth in the subject.

12. The method according to claim 7, wherein the mixture is made of carnitine, caffeine, arginine as active principle according to the following concentrations: carnitine from 1.0 to 33.3 mg/ml, caffeine from 1.0 to 33.3 mg/ml, arginine from 3 to 100 mg/ml, and it is administered topically.

13. The method according to claim 7, wherein the mixture is made of carnitine, caffeine, arginine as active principle according to a daily administration dose within the following ranges: carnitine 4-400 mg, caffeine 4-400 mg, arginine 12-1200 mg, and it is administered orally.

* * * * *